United States Patent
Majeed et al.

(10) Patent No.: US 10,966,919 B2
(45) Date of Patent: Apr. 6, 2021

(54) **ANTI-AGING POTENTIAL OF EXTRACELLULAR METABOLITE ISOLATED FROM *BACILLUS COAGULANS* MTCC 5856**

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN); Lakshmi Mundkur, Bangalore (IN); Shaheen Majeed, Springville, UT (US)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN); Lakshmi Mundkur, Bangalore (IN); Shaheen Majeed, Springville, UT (US)

(73) Assignee: SAMI LABS LIMITED, Bangalore (IN)

(*) Notice: Subject to any disclaimer, the term of this patent is extended or adjusted under 35 U.S.C. 154(b) by 341 days.

(21) Appl. No.: 15/996,791

(22) Filed: Jun. 4, 2018

(65) Prior Publication Data
US 2018/0344628 A1 Dec. 6, 2018

Related U.S. Application Data

(60) Provisional application No. 62/516,083, filed on Jun. 6, 2017, provisional application No. 62/516,077, filed on Jun. 6, 2017.

(51) Int. Cl.
*A61K 8/99* (2017.01)
*A61Q 19/08* (2006.01)
*A61P 17/00* (2006.01)

(52) U.S. Cl.
CPC ............ *A61K 8/99* (2013.01); *A61P 17/00* (2018.01); *A61Q 19/08* (2013.01)

(58) Field of Classification Search
CPC ...... A61K 8/99; A61K 35/742; A61K 47/183; A61K 47/32; A61K 47/44; A61K 9/0014; A61K 2800/782; A61P 17/00; A61P 17/08; A61P 17/14; A61Q 19/08; A61Q 7/00; A61Q 5/00
See application file for complete search history.

(56) References Cited

U.S. PATENT DOCUMENTS 6,905,692 B2 * 6/2005 Farmer .............. A61K 9/0014 424/260.1
9,596,861 B2 * 3/2017 Majeed .................... C12R 1/42

OTHER PUBLICATIONS

Sharma D, Kober MM and Bowe WP, Anti-Aging Effects of Probiotics, J Drugs Dermatol. Jan. 2016; 15(1):9-12.
Benedetta Cinque, Paola Palumbo, Cristina La Torre, Esterina Melchiorre, Daniele Corridoni, Gianfranca Miconi, Luisa Di Marzio, Maria Grazia Cifone and Maurizio Giuliani, Probiotics in Aging Skin, Textbook of Aging Skin, 2010, pp. 1315-1327.
Probiotics Provide Anti Aging Defense, Life Extension Magazine, Oct. 2015 http://www.lifeextension.com/Magazine/2015/10/Probiotics-Provide-Anti-Aging-Defense/Page-01, accessed May 24, 2018, 11 pages.
Katie Schaefer, Anti-aging Probiotic from Bacillus coagulans, https://www.cosmeticsandtoiletries.com/formulating/function/active/142099203.html, Mar. 9, 2012, accessed May 26, 2018, 1 pg.
Guidelines for the evaluation of probiotics in food, Joint FAO/WHO Working Group Report on Drafting Guidelines for the Evaluation of Probiotics in Food, London, Ontario, Canada, Apr. 30 and May 1, 2002, See section 3.1, indicating that The current state of evidence suggests that probiotic effects are strain specific, 11 pages.
Probiotics: In Depth/NCCIH, U.S. Department of Health and Human Services (http://www.hhs.gov/) National Institutes Health (http://www.nih.gov/), Aug. 2019, 16 pages.
Indian Council of Medical Research/Department of Biotechnology, Ministry of Science and Technology, Government of India, New Delhi), ICMR-DBT Guidelines for Evaluation of Probiotics in Food, 2011), Section 2, Subsection 2.3), pp. (i)-(vii) and 1-11.
Mannu et al. (2003) International Journal of Food Microbiology 88 (2003) 291-304.
Valentus "ProDURA® Bacillus coagulans Demonstrates Superior Heat Resistance", <URL: http://valentuschoice.com/ProDura-Comparison.pdf; https://earthnutri.com/pages/produra%C2%AE>, Archived online Aug. 2020, 4 pages.

* cited by examiner

*Primary Examiner* — Aaron J Kosar

(57) ABSTRACT

Disclosed is the use of partially purified extracellular metabolite isolated from *Bacillus coagulans* MTCC 5856 to prevent skin aging. More specifically the invention discloses the anti-collagenase, anti-elastase, anti-glycation activity and enhancement of TGF-β, epidermal growth factor and hyaluronic acid expression in human dermal fibroblasts, of extracellular metabolites isolated from *Bacillus coagulans* MTCC 5856.

11 Claims, 2 Drawing Sheets

Specification includes a Sequence Listing.

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Forward Primer of h has

<400> SEQUENCE: 1
tgtgactcgg acacaaggtt g                                      21
```

```
<210> SEQ ID NO 2
<211> LENGTH: 19
<212> TYPE: DNA
<213> ORGANISM: Artificial Sequence
<220> FEATURE:
<223> OTHER INFORMATION: Reverse primer of h has

<400> SEQUENCE: 2
gcctaagaaa ctgctgcaa                                              19

<210> SEQ ID NO 3
<211> LENGTH: 19
<212> TYPE: DNA
<213> ORGANISM: Artificial Sequence
<220> FEATURE:
<223> OTHER INFORMATION: Forward primer of H TGF beta

<400> SEQUENCE: 3
cccagcatct gcaaagctc                                              19

<210> SEQ ID NO 4
<211> LENGTH: 20
<212> TYPE: DNA
<213> ORGANISM: Artificial Sequence
<220> FEATURE:
<223> OTHER INFORMATION: Reverse primer of H TGF beta

<400> SEQUENCE: 4
gtcaatgtac agctgccgca                                             20

<210> SEQ ID NO 5
<211> LENGTH: 20
<212> TYPE: DNA
<213> ORGANISM: Artificial sequence
<220> FEATURE:
<223> OTHER INFORMATION: Forward primer of hEGF

<400> SEQUENCE: 5
ctcaaggaat cggctgggga                                             20

<210> SEQ ID NO 6
<211> LENGTH: 20
<212> TYPE: DNA
<213> ORGANISM: Artificial sequence
<220> FEATURE:
<223> OTHER INFORMATION: Reverse Primer of hEGF

<400> SEQUENCE: 6
cagtcaaaga tcctggagca                                             20
```

ANTI-AGING POTENTIAL OF EXTRACELLULAR METABOLITE ISOLATED FROM *BACILLUS COAGULANS* MTCC 5856

CROSS-REFERENCE TO RELATED PATENT APPLICATION

The present invention is non-provisional filing of U.S. provisional patent application Nos. 62/516,083 filed on 6 Jun. 2017 and 62/516,077 filed on 6 Jun. 2017.

FIELD OF THE INVENTION

The invention in general relates to biological applications of extracellular metabolite isolated from *Bacillus coagulans* MTCC 5856. More specifically, the present invention discloses the anti-aging potential of extracellular metabolite isolated from *Bacillus coagulans* MTCC 5856.

DESCRIPTION OF PRIOR ART

With increase in age, the human skin is subjected to many changes which include wrinkling, sagging and increased laxity that visibly reveal the signs of aging. There are many intrinsic and extrinsic factors that affect skin aging such as hormones, skin-associated microflora, skin pH, reduced stratum corneum lipid content, decreased absolution of reactive oxygen species (ROS), greater metalloproteinase activity, desiccation, laxity, fine wrinkles, and atrophy of the skin, Of the above factors, many are natural and cannot be altered. There are several other factors that cause premature skin aging and can be influenced to induce graceful skin aging.

Prevention of skin aging is now being targeted widely by the industry players in the field of cosmetics and there is now an increased requirement for natural products that prevent skin aging. Probiotics are now being currently used in the skin care industry due to the health benefits they provide. The role of probiotics in aging, beauty, photodamage, and skin health are well described in the following prior art documents:
1. Sharma D, Kober M M and Bowe W P, Anti-Aging Effects of Probiotics, J Drugs Dermatol. 2016 January; 15(1):9-12
2. Benedetta Cinque, Paola Palumbo, Cristina La Torre, Esterina Meichiorre, Daniele Corridoni, Gianfranca Miconi, Luisa Di Marzio, Maria Grazia Cifone and Maurizio Giuliani, Probiotics in Aging Skin, Textbook of Aging Skin, pp. 1315-1327
3. Probiotics Provide Anti Aging Defense, LIFE EXTENSION MAGAZINE, October 2015 lifeextension.com/Magazine/2015/10/Probiotics-Provide-Anti-Aging-Defense/Page-01, accessed 24 May 2018.

Both probiotics and their extracellular metabolites are now being incorporated into skin care products (Katie Schaefer, Anti-aging Probiotic from *Bacillus coagulans*, cosmeticsandtoiletries.com/formulatingfunction/active/142099203.html, Mar. 9, 2012, accessed 26 May 2018). However, it is well known in the scientific art that biological effects of probiotics or products thereof are strain specific and cannot be generalised among genera, species and strains (Probiotics: In Depth/NCCIH, U.S. Department of Health and Human Services, National Institutes of Health). Hence, there exists a need to find a superior probiotic strain and its extracellular product that can used effectively to reduce all signs of skin aging. The present invention solves the above mentioned problem by disclosing the beneficial effects of partially purified extracellular metabolite preparation of *Bacillus coagulans* on reducing skin aging.

It is the principle objective of the invention to disclose the anti-aging activity of a composition containing extracellular metabolite preparation of *Bacillus coagulans* MTCC 5856 by inhibiting the activities of collagenase and elastase and increasing the expression of TGF-$\beta$, epidermal growth factor and hyaluronic acid.

It is another objective of the invention to disclose the anti-glycation activity of a composition containing extracellular metabolite preparation of *Bacillus coagulans* MTCC 5856.

The present invention fulfills the above mentioned objectives and provides further related advantages.

Deposit of Biological Material

The deposit of biological material *Bacillus coagulans* bearing accession number MTCC 5856, mentioned in the instant application has been, made on 19 Sep. 2013 at Microbial Type Culture Collection & Gene Bank (MTCC), CSIR-Institute of Microbial Technology, Sector 39-A, Chandigarh—160036, India. The deposited material has been accepted for deposit under the Budapest Treaty on International Recognition of the Deposit of Micro-organism for the purpose of Patent procedure and that all restrictions on the availability to the public of the material so deposited will be irrevocably removed upon granting of the patent.

SUMMARY OF THE INVENTION

The present invention discloses the ability of partially purified extracellular metabolite isolated from *Bacillus coagulans* MTCC 5856 to prevent skin aging. More specifically the invention discloses the anti-collagenase, anti-elastase, anti-glycation activity and enhancement of TGF-$\beta$, epidermal growth factor and hyaluronic acid expression in human dermal fibroblasts, of extracellular metabolites isolated from *Bacillus coagulans* MTCC 5856.

DESCRIPTION OF THE MOST PREFERRED EMBODIMENTS

Figure 1:
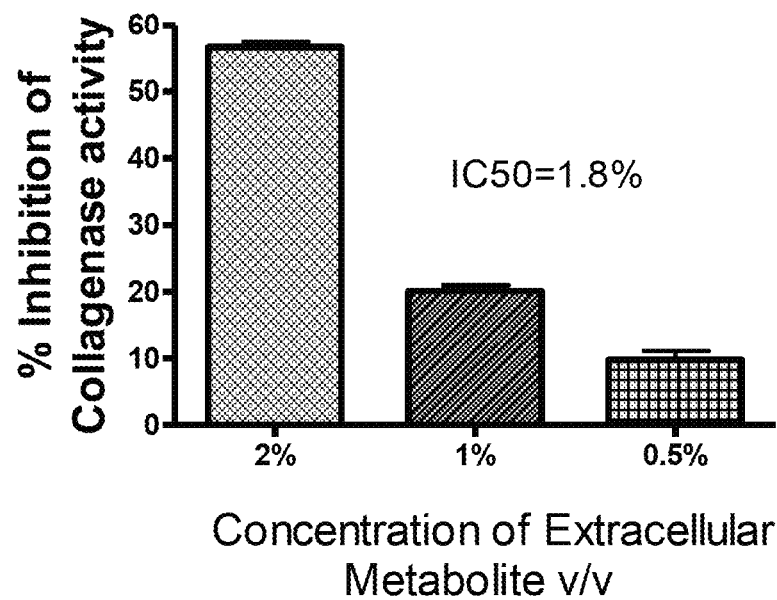
FIG. 1 is graphical representation of the % inhibition of collagenase activity by the partially purified extracellular metabolite isolated from *Bacillus coagulans* MTCC 5856.

In the most preferred embodiment, the present invention discloses a method of preventing skin aging in mammals, said method comprising step of administering effective concentration of a composition containing partially purified extracellular metabolite isolated from *Bacillus coagulans* to said mammals to bring about a reduction in signs and symptoms of skin aging. In a related embodiment, the signs and symptoms of skin aging is selected from the group consisting of wrinkles, sagging of skin, dryness, patchy skin, and lines. In another related embodiment, skin aging is prevented by inhibiting the activity of the enzymes collagenase and elastase, inhibiting glycation and enhancing the expression of TGF-β, epidermal growth factor and hyaluronic acid. In another related embodiment, the strain of *Bacillus coagulans* is *Bacillus coagulans* MTCC 5856. In another related embodiment, the effective concentration of the partially purified extracellular metabolite preparation is 0.01% v/v to 2.0% v/v of the total composition. In yet another related embodiment the composition is formulated with pharmaceutically/cosmeceutically acceptable excipients, adjuvants, bases, diluents, carriers, conditioning agents, bioavailability enhancers, antioxidants and preservatives and/or incorporated into formulations containing anti-aging ingredients and administered topically in the form of creams, gels, lotions, powder, serum, oil, suspensions, ointments, soaps, scrubs, emulsions, and compacts. In a related embodiment, the mammal is preferably human.

In another aspect, the present invention relates to a method of inhibiting collagenase activity in skin fibroblasts, said method comprising steps of bringing into contact said fibroblast cells with effective concentration of a composition containing partially purified extracellular metabolite preparation from *Bacillus coagulans*, to bring about effect of collagenase inhibition therein. In another related embodiment, the effective concentration of the partially purified extracellular metabolite preparation is 0.01% v/v to 2.0% v/v of the total composition. In another related embodiment, the strain of *Bacillus coagulans* is *Bacillus coagulans* MTCC 5856.

In another preferred embodiment, the invention relates to a method of inhibiting elastase activity in skin fibroblasts, said method comprising steps of bringing into contact said fibroblast cells with effective concentration of extracellular metabolite preparation from *Bacillus coagulans* MTCC 5856, to bring about effect of elastase inhibition therein. In another related embodiment, the effective concentration of the partially purified extracellular metabolite preparation is 0.01% v/v to 2.0% v/v of the total composition. In another related embodiment, the strain of *Bacillus coagulans* is *Bacillus coagulans* MTCC 5856.

In another preferred embodiment, the invention relates to a method of inhibiting glycation in skin fibroblasts, said method comprising steps of bringing into contact said fibroblast cells with effective concentration of extracellular metabolite preparation from *Bacillus coagulans* MTCC 5856, to bring about the effect of anti-glycation therein. In another related embodiment, the effective concentration of the partially purified extracellular metabolite preparation is 0.01% v/v to 2.0% v/v of the total composition. In another related embodiment, the strain of *Bacillus coagulans* is *Bacillus coagulans* MTCC 5856.

In another preferred embodiment, the invention relates to a method of enhancement of TGF-β, epidermal growth factor and hyaluronic acid expression in human dermal fibroblasts, said method comprising steps of bringing into contact said fibroblast cells with effective concentration of extracellular metabolite preparation from *Bacillus coagulans* MTCC 5856, to bring about the increased expression of genes related to anti-ageing effect.

Specific illustrative examples enunciating the most preferred embodiments are included herein below Example 1: Anti Collagenase Activity Isolation of Extracellular Metabolite The extracellular metabolite from *Bacillus coagulans* MTCC 5856 was isolated as per the steps outlined in U.S. Pat. No. 9,596,861. The product is commercially available under the trade name LACTOSPORIN® (INCI: *Bacillus* ferment filtrate extract) from Sabinsa Corporation, USA.

Materials and Methods

Collagenase is one of the matrix metalloprotease, which digest collagen and other components of the extra cellular matrix (ECM). The ECM serves as a scaffold to stabilize the skin structure, and also helps in proliferation and metabolic functions of the skin cells. Loss of collagen leads to wrinkles and sagging of skin. The principle of the assay of collagenase inhibition is based on the fact that the substrate DQ™ gelatine is conjugated to fluorecein—a fluorescent compound. In DQ™ gelatine, fluorescence is quenched. DQ™ gelatine is efficiently digested by collagenases to yield a fluorescent compound which can be measured. The increase in fluorescence is proportional to enzyme activity. In the presence of an anti collagenase compound the amount of fluorescence will be decreased for a fixed concentration of enzyme and substrate.

Materials

Equipment-BMG FLUOstar Optima (fluorescent Microplate reader)

Reagents: Phosphate buffer (pH 7.4)

Collagenase Enzyme assay kit (Enzchek® collagenase, gelatinase assay kit, Invitrogen, USA)

Microtitre plates—96 well microtitre plates (black)—Corning. USA

The assay was performed in a 96 well black microtitre plate. Type IV from *Clostridium histolyticum* with DQ gelatin as substrate was used for the assay. Different concentrations of LACTOSPORIN® (80 µl) were pre incubated with 20 µl of gelatin substrate (12.5 µg/ml). 100 µl of the Collagenase enzyme solution (final concentration-0.4 U/ml) was added and the fluorescence intensity was measured at Em: 485 nm and Ex: 520 nm after 30 minutes. Enzyme activity of control (buffer) was recorded The percentage inhibition is calculated as follows:—

$$\% \text{ Inhibition} = \frac{(B - BC) - (T - C)}{(B - BC)} \times 100$$

B—Fluorescence in the presence of enzyme.
BC—Fluorescence in the absence of enzyme activity
T—Fluorescence of enzyme activity in the presence of inhibitor
TC—Fluorescence of the inhibitor alone Results The extracellular metabolite exhibited a dose dependent anti collagenase activity with an $IC_{50}$ at 1.8% (50% inhibition of enzyme activity) (FIG. 1). The results revealed that the extracellular metabolite isolated from *Bacillus coagulans* MTCC 5856 can preserve the extracellular matrix of the skin and prevent wrinkle formation and skin sagging, thereby preventing skin aging.

Example 2: Anti Elastase Activity

Isolation of Extracellular Metabolite

The extracellular metabolite from *Bacillus coagulans* MTCC 5856 was isolated as per the steps outlined in U.S. Pat. No. 9,596,861. The product is commercially available under the trade name LACTOSPORIN® (INCI: *Bacillus* ferment filtrate extract) from Sabinsa Corporation, USA.

Materials and Methods

Elastase is one of the matrix metalloproteinases, which digest elastin and other components of the extra cellular matrix and is important both for normal skin development. If this enzyme is not regulated by inhibitor proteins results in wrinkling of skin, premature ageing and carcinogenesis. The Anti-Elastase assay by Enz Chek elastase assay kit determines the elastase inhibitory activity of the products. The assays were done using the EnzChek elastase assay kit. The substrate is DQ elastin soluble bovine neck ligament. DQ elastin is labeled with BODIPY FL dye. The non-fluorescent substrate can be digested by elastase to yield highly fluorescent fragments and in the presence of inhibitor, the fluorescence intensity is quenched. The fluorescence intensity was measured in a microplate reader (emission at 485 nm and excitation at 520 nm.)

Materials

Equipment—BMG FLUOstar Optima (fluorescent Microplate reader)
Reagents: Phosphate buffer (pH 7.4)
Collagenase Enzyme assay kit (Enzchek® collagenase, gelatinase assay kit, Invitrogen, USA)
Microtitre plates—96 well microtitre plates (black)—Corning, USA The assay was performed in a 96 well black microtitre plate. Elastase enzyme from pig pancreas and DQ Elastin as substrate was used for the assay. Different concentrations of LACTOSPORIN® (50 µl) were pre incubated with 50 µl of elastin substrate (25 µg/ml). 100 µl of the Elastase enzyme solution (final concentration—0.1 U/ml) was added and the fluorescence intensity was measured at Em: 485 nm and Ex: 520 nm after 30 minutes. Enzyme activity of control (buffer) was recorded The percentage inhibition is calculated as follows:—

$$\% \text{ Inhibition} = \frac{(B - BC) - (T - C)}{(B - BC)} \times 100$$

Figure 2:
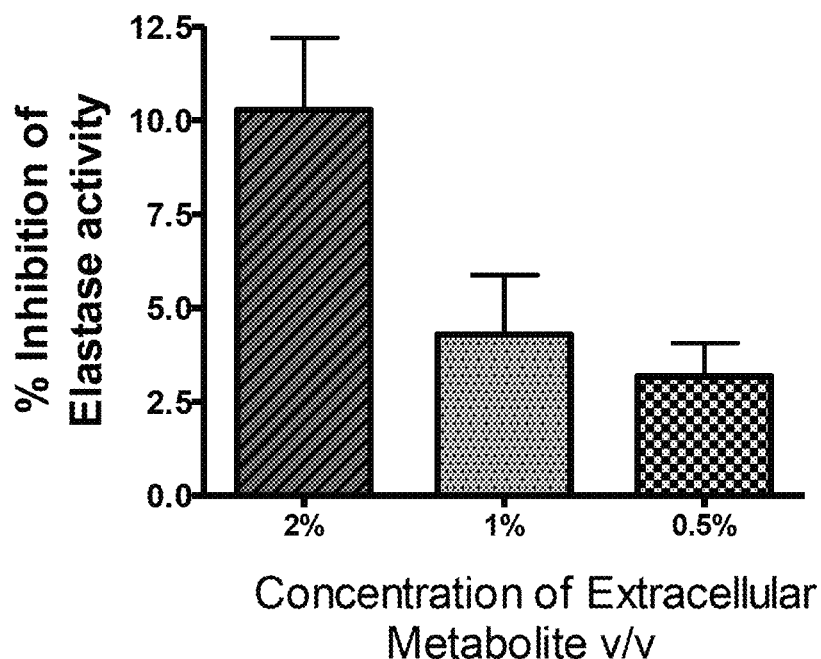
FIG. 2 is graphical representation of the % inhibition of elastase activity by the partially purified extracellular metabolite isolated from *Bacillus coagulans* MTCC 5856.
Figure 3:
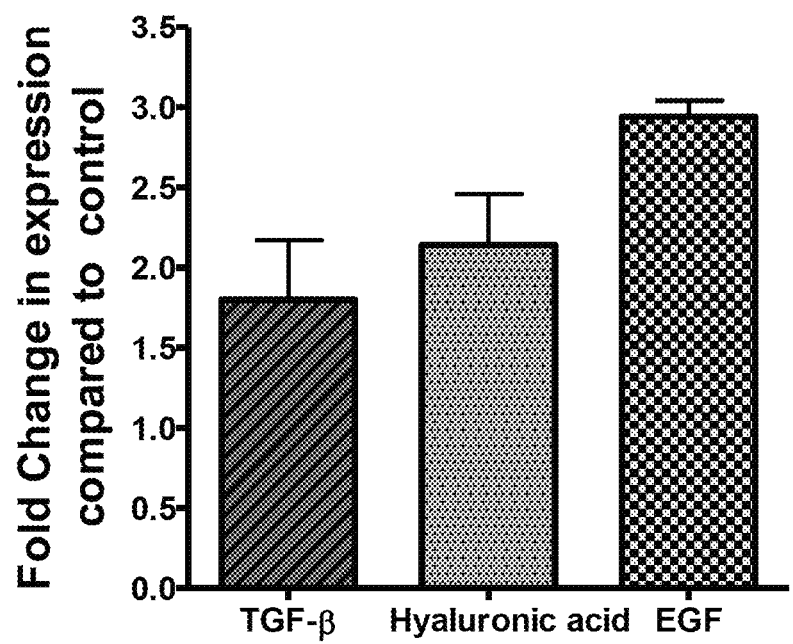
FIG. 3 is graphical representation of the increased expression of TGF-$\beta$, epidermal growth factor and hyaluronic acid in human dermal fibroblasts by the partially purified extracellular metabolite isolated from *Bacillus coagulans* MTCC 5856.

B—Fluorescence in the presence of enzyme
BC—Fluorescence in the absence of enzyme activity
T—Fluorescence of enzyme activity in the presence of inhibitor
TC—Fluorescence of the inhibitor alone Conclusion The extracellular metabolite exhibited a dose dependent anti elastase activity with an $IC_{50}$ at 1.8% (50% inhibition of enzyme activity) (FIG. 2). The results revealed that the extracellular metabolite isolated from *Bacillus coagulans* MTCC 5856 can preserve the extracellular matrix of the skin and prevent wrinkle formation and skin sagging, by inhibiting the enzyme elastase, thereby preventing skin aging.

Example 3: Anti-Glycation

Isolation of Extracellular Metabolite

The extracellular metabolite from *Bacillus coagulans* MTCC 5856 was isolated as per the steps outlined in U.S. Pat. No. 9,596,861. The product is commercially available under the tradename LACTOSPORIN® (INCI: *Bacillus ferment filtrate extract*) from Sabinsa Corporation, USA.

Materials and Methods

Advanced glycation end products (AGEs) are generated by the non enzymatic adduct formation between amino groups of proteins (predominantly lysine and arginine) and carbonyl groups of reducing sugar, also known as Maillard reaction. In the early stages, reducing sugars react with free amino groups to form an unstable aldimine compound which undergoes molecular rearrangement to form a stable early glycation product known as Amadori product. In the later stages, glycation process through oxidation, dehydration and cyclization reactions forms the advanced glycation end products also known as AGE. Various structures of AGEs such as Nε-(carboxymethyl)-lysine (CML), pyrraline, pentosidine, are known to be associated with degenerative disorders, including aging, diabetes, atherosclerosis Alzheimer's disease, and renal failure. AGEs also implicated in skin aging, accumulate a result of UV irradiation in both senescent and photoaged skin.

AGE can be fluorescent as well as non fluorescent in nature. Typically the vesperlysine type of AGE with typical structure as shown below have an excitation at 370-nm and emission at 440 nm, while pentosidine like AGE have an excitation at 335 nm and emission at 385 nm. The principle is based on the fact that ribose sugar and bovine serum albumin are mixed in specific ratio and incubated for 24 hours. Vesperlysine like AGE formed by the reaction was estimated by the increase in fluorescence detected at Ex/Em at 390/460 nm and pentosidines were detected at Ex/Em at 320/405 nm Materials Ribose, Bovine serum albumin, 96 well black microtitre plates Ribose—BSA method: 10 µl of various concentrations of samples were added to 40 µl of BSA (bovine serum albumin, 25 mg/ml stock) and 50 µl of D-Ribose (150 mg/ml stock) was added per well of black 96-well microplate and incubated for 24 h at 37° C. Sample with only BSA is taken as the control. The AGE (advanced glycation end product) formed were detected by the fluorescence at Ex/Em at 390/460 nm for vesperlysine and Ex/Em at 320/405 nm for pentosidine AGE.

Results

The inhibition of the AGEs vesperlysine and Pentosidine by the extracellular metabolite preparation from *Bacillus coagulans* MTCC 5856 is tabulated in table 1.

TABLE 1

| Percentage inhibition of AGEs by extracellular metabolite preparation from *Bacillus coagulans* | | |
|---|---|---|
| Conc. Of extracellular metabolite preparation (%) | % Inhibition of vesperlysine Ex/Em at 390/460 nm | % Inhibition of pentosidine Ex/Em at 320/405 nm |
| 2% | 86.87 ± 3.09 | 41.75 ± 1.48 |
| 1% | 60.78 ± 3.35 | 34.26 ± 1.89 |
| 0.50% | 39.58 ± 2.60 | 28.14 ± 1.85 |
|  | IC50 = 0.7% | IC50 = 2.89% |

Results

The extracellular metabolite preparation from *Bacillus coagulans* MTCC 5856 showed significant inhibition of vesperlysine type advanced glycation end product formation with 50% inhibition at 0.7%. Also, the metabolite was found to inhibit pentosidine type AGE formation by 41.75% at a concentration of 2%, indicating that the extracellular metabolite preparation from *Bacillus coagulans* MTCC 5856 has the ability to preventing different types of glycation end products and thus can protect against the destructive effects of glycation and help boost the skin's healing and thereby prevent skin aging.

Example 4: Gene Expression

Isolation of Extracellular Metabolite

The extracellular metabolite from *Bacillus coagulans* MTCC 5856 was isolated as per the steps outlined in U.S. Pat. No. 9,596,861. The product is commercially available under the trade name LACTOSPORIN® (INCI: *Bacillus* ferment filtrate extract) from Sabinsa Corporation, USA.

Materials and Methods

Dermal fibroblasts are crucial cellular components for the structural integrity of the skin. The extracellular matrix contains collagen, elastin and hyaluron which determine the integrity of skin. Hyaluronan (HA) synthesized by hyaluronan synthases which add UDP-glucosamine and UDP-glucuronic acid residues to a growing HA polymer chain. Transforming growth factor (TGF)-β plays a central role in ECM biosynthesis and controls collagen homeostasis by regulation of both collagen synthesis and degradation. Epidermal growth factor stimulates cell growth and induces collagen synthesis.

Materials: Human dermal fibroblast cells, 6 well microtiter plays, fibroblast growth media, Trizol, can synthesis kit, SYBR green master mix for RT-PCR Methods:

Human dermal fibrobalsts were cultured in 6 well microtitre plates in the presence of 0.25% extracellular metabolite from *Bacillus coagulans* MTCC 5856 for 24 hours. Untreated cells were used as control. At the end of incubation time, the cells were lysed and RNA was extracted RNA Extraction Cells were harvested after second progression on day 7 and total RNA was extracted using the Trizol method. Extracted RNA was treated with DNAse I to remove any contaminating DNA and again extracted using phenol:chloroform:isoamyl alcohol extraction (24:25:1). Quality of RNA was determined by checking the absorbance at 260/280 nm using a Nanodrop (Thermo)

Quantitative Real Time PCR

2 μg of total RNA was taken for cDNA synthesis using SuperScript III First-Strand Synthesis System (Life Technologies). Quantitative RT-PCR analysis was performed to determine the expression of brown fat specific genes in Roche Light cycler 96 using SYBR Green master mix (Thermo Scientific). β actin was used as a house keeping gene The relative RNA abundance of the genes was normalized to the housekeeping β actin gene and expressed as delta delta CT (equivalent to fold change transformed by $Log_2$). Table 2 indicates the list of primers used for the expression studies.

TABLE 2

Primer sequences

| Name | Primer sequence |
|---|---|
| BAT specific Genes | |
| h has F | TGTGACTCGGACACAAGGTTG |
| h has R | GCCTAAGAAACTGCTGCAA |
| H TGF-β-F | CCCAGCATCTGCAAAGCTC |
| H TGF-β-R | GTCAATGTACAGCTGCCGCA |
| hEGF F | CTCAAGGAATCGGCTGGGGA |
| hEGF R | CAGTCAAAGATCCTGGAGCA |

Results

The extracellular metabolite preparation from *Bacillus coagulans* MTCC 5856 showed significant enhancement of the hyaluronic acid synthase, (2.14 fold) transforming growth factor (TGF)-β (1.8 fold) and epidermal growth factor (2.94 fold) in human dermal fibroblasts, indicating that the extracellular metabolite preparation from *Bacillus coagulans* MTCC 5856 has the ability to increase the expression of genes related to maintaining the integrity of extracellular matrix. The extracellular matrix (ECM) that provides structure and support for the skin cells and confers tensile strength and firmness to the skin thus making the skin look younger.

Example 5: Formulations Containing Extracellular Metabolite Preparation from *Bacillus coagulans* for the Prevention of Skin Aging The composition containing the extracellular metabolite from *Bacillus coagulans* MTCC 5856 may be formulated with pharmaceutically/cosmeceutically acceptable excipients, adjuvants, bases, diluents, carriers, conditioning agents, bioavailability enhancers, antioxidants and preservatives and/or incorporated into formulations containing anti-aging ingredients and administered topically in the form of creams, gels, lotions, powder, serum, oil, suspensions, ointments, soaps, scrubs, emulsions, and compacts.

In a related aspect, one or more anti-aging skin care ingredients are selected from the group consisting of, but not limited to, Alpha Lipoic Acid, oxyresveratrol, Beet root extract, *Boswellia serrata* Extract, β boswellic acids, *Boswellia serrata* oil, *Centella asiatica* Extract, triterpenes, *Garcinia indica* extract, anthocyanins, *Cocos nucifera* extract and juice, *Coleus forskohlii* Extract, forskolin, *Coleus forskohlii* Oil, Tetrahydropiperine, Ellagic Acid, Gallnut Extract, polyphenols, Galanga Extract, Glycyrrhizinic Acid, Green Tea Extract, Epigallocatechin Gallate, Licorice extract, MonoAmmonium Glycyrrhizinate, Limonoids, Oleanolic Acid, Cosmetic peptides (Oleanolic acid linked to Lys-Thr-Thr-Lys-Ser, Oleanolic acid linked to Lys-Val-Lys), Oleuropein, Piper longumine extract, piperine, Ellagic acid, Pomegranate Extract (Water Soluble), pterostilbene, resveratrol, *Pterocarpus santalinus* extract, Rosemary Extract, Rosmarinic Acid, Amla extract, beta glucogallin, tetrahydrocurcumin, *Salvia officinalis* (Sage) Leaf Extract, Ursolic Acids, Saponins, *Sesamum indicum* (Sesame) Seed Extract, Sesamin and sesamolin, moringa oil, moringa seed extract, Horse Chestnut Extract, Vitex Oil, Xymenynic Acid, ethyl ascorbic acid, Argan oil, Lemon peel extract, turmeric oil, Barley Beta Glucans, coenzyme Q10, olive oil, avocado oil and cranberry oil.

In another related aspect, one or more anti-oxidants and anti-inflammatory agents are selected from the group consisting of, but not limited to, vitamin A, D, E, K, C, B complex, rosmarinic acid, Alpha Lipoic Acid, oxyresveratrol, Ellagic Acid, Glycyrrhizinic Acid, Epigallocatechin Gallate, plant polyphenols, Glabridin, moringa oil, oleanolic acid, Oleuropein, Carnosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosyl-rutin, calalase and the superoxide dismutase, glutathione, selenium compounds, butylated hydroxyanisole (BHA), butylated hydroxytoluene (BHT), sodium metabisulfite (SMB), propyl gallate (PG) and amino acid cysteine.

In another related aspect, one or more bioavailability enhancers are selected from the group, but not limited to, piperine, tetrahydropiperine, quercetin, Garlic extract, ginger extract, and naringin.

Tables 3-7 provide illustrative examples of anti-aging skin care formulations containing partially purified extracellular metabolite preparation from *Bacillus coagulans* MTCC 5856 (*Bacillus* ferment filtrate extract)

TABLE 3

Anti-aging serum

Active Ingredients

*Bacillus* ferment filtrate extract 0.01%-2%
Cosmetic peptide (Olepent ®*), Tetrahydrocurcumin, *Cocos nucifera* (Coconut) Fruit Juice, Turmeric Oil, Argan oil, Lipactive IncaInchi ®#

Other ingredients/Excipients

Chelating agents, Humectants, Conditioning agents, Emulsifiers, Antioxidants, Preservatives, Thickeners (Like Cellulose derivatives, Acrylates Crosspolymer, Acrylates/C10-30 Alkyl Acrylate Cross Polymer, Carbomers), Neutralising agents, Fragrance, Bioavailability enhancers

*Registered Trademark of Sabinsa Corporation
Registered Trademark of Greentech

TABLE 4

Anti-Aging Cleanser

Active Ingredients

*Bacillus* ferment filtrate extract 0.01%-2%
Cosmetic peptide (Olepent ®*), Tetrahydrocurcumin, *Cocos nucifera* (Coconut) Fruit Juice, Turmeric Oil, Argan oil, Lipactive IncaInchi ®#

Other ingredients/Excipients

Niacinamide, lemon peel extract, Vitamin E acetate, Bioavailability enhancers (Piperine extract or Tetrahydropiperine (Cosmoperine ®)), Chelating agents, Humectants, Non-Ionic Surfactants (Like Lauryl Glucoside, Decyl Glucoside, Coco Glucoside, Amphoteric), Emulsifiers, Antioxidants, Preservatives, Thickeners (Like Cellulose derivatives, Acrylates Crosspolymer, Acrylates/C10-30 Alkyl Acrylate Cross Polymer, Carbomers), Neutralising agents, Fragrance.

*Registered Trademark of Sabinsa Corporation
Registered Trademark of Greentech

TABLE 5

Anti-aging balancing toner

Active Ingredients

*Bacillus* ferment filtrate extract 0.01%-2%
Cosmetic peptide (Olepent ®*), Tetrahydrocurcumin, *Cocos nucifera* (Coconut) Fruit Juice, Turmeric Oil, Argan oil, Lipactive IncaInchi ®#

Other ingredients/Excipients

Tetrahydropiperine (Cosmoperine ®), Chelating agents, Humectants, Emulsifiers, Antioxidants, Preservatives, Thickeners (Like Cellulose TABLE 5-continued Anti-aging balancing toner derivatives, Acrylates Crosspolymer, Acrylates/C10-30 Alkyl Acrylate Cross Polymer, Carbomers), Neutralising agents (if required), Fragrance.

*Registered Trademark of Sabinsa Corporation
Registered Trademark of Greentech

TABLE 6

Anti-aging Moisturizer

Active Ingredients

*Bacillus* ferment filtrate extract 0.01%-2%
Cosmetic peptide (Olepent ®*), Tetrahydrocurcumin, *Cocos Nucifera* (Coconut) Fruit Juice, Turmeric Oil, Argan oil, Lipactive IncaInchi ®#

Other ingredients/Excipients

Barley Beta Glucans, niacinamide, policosanol, *Amaranthus* extract, Avocado Butter & *Macademia* oil Tetrahydropiperine (Cosmoperine ®)), Chelating agents, Humectants, Emulsifiers, Antioxidants, Preservatives, Thickeners (Like Cellulose derivatives, Acrylates Crosspolymer, Acrylates/C10-30 Alkyl Acrylate Cross Polymer, Carbomers), Neutralising agents (if required), Fragrance and silicones

*Registered Trademark of Sabinsa Corporation
Registered Trademark of Greentech

TABLE 7

Anti-aging Cream

Active Ingredients

*Bacillus* ferment filtrate extract 0.01%-2%
Coenzyme Q10, Cosmetic peptide (Olepent ®*), Tetrahydrocurcumin, *Boswellia serrata* extract Other ingredients/Excipients Galanga extract, D-Panthenol, Bisabolol, Tetrahydropiperine (Cosmoperine ®)), Chelating agents, Humectants, Emulsifiers, Antioxidants, Preservatives, Thickeners (Like Cellulose derivatives, Acrylates Crosspolymer, Acrylates/C10-30 Alkyl Acrylate Cross Polymer, Carbomers), Neutralising agents (if required), Fragrance, silicones, Olive Oil, Avacado Oil and Cranberry Oil The above formulations are merely illustrative examples; any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method of therapeutic management of skin aging in mammals, said method comprising step of administering effective concentration of a composition comprising partially purified extracellular metabolite isolated from *Bacillus coagulans* MTCC 5856 to mammals in need of such therapeutic management.

2. The method as in claim 1, wherein management of skin aging is brought about by inhibiting the activity of the enzymes collagenase and elastase, inhibiting glycation and enhancing the expression of TGF-β, epidermal growth factor and hyaluronic acid.

3. The method as in claim 1, wherein the effective concentration of the partially purified extracellular metabolite preparation is 0.01% v/v to 2.0% v/v of the total composition.

4. The method as in claim 1, wherein the composition is formulated with pharmaceutically/cosmeceutically acceptable excipients, adjuvants, bases, diluents, carriers, conditioning agents, bioavailability enhancers, antioxidants and preservatives and/or incorporated into formulations containing anti-aging ingredients and administered topically in the form of creams, gels, lotions, powder, serum, oil, suspensions, ointments, soaps, scrubs, emulsions, and compacts.

5. The method as in claim 1, wherein the mammal is human.

6. A method of inhibiting collagenase activity in skin fibroblasts, said method comprising steps of bringing into contact said fibroblast cells with effective concentration of a composition containing partially purified extracellular metabolite preparation from *Bacillus coagulans* MTCC 5856, to bring about effect of collagenase inhibition therein.

7. The method as in claim 6, wherein the effective concentration of the partially purified extracellular metabolite preparation is 0.01% v/v to 2.0% v/v of the total composition.

8. A method of inhibiting elastase activity in skin fibroblasts, said method comprising steps of bringing into contact said fibroblast cells with effective concentration of extracellular metabolite preparation from *Bacillus coagulans* MTCC 5856, to bring about effect of elastase inhibition therein.

9. The method as in claim 8, wherein the effective concentration of the partially purified extracellular metabolite preparation is 0.01% v/v to 2.0% v/v of the total composition.

10. A method of inhibiting glycation in skin fibroblasts, said method comprising steps of bringing into contact said fibroblast cells with effective concentration of extracellular metabolite preparation from *Bacillus coagulans* MTCC 5856, to bring about the effect of anti-glycation therein.

11. The method as in claim 10, wherein the effective concentration of the partially purified extracellular metabolite preparation is 0.01% v/v to 2.0% v/v of the total composition.

* * * * *